United States Patent [19]

Jacobsen et al.

[11] Patent Number: 5,391,371
[45] Date of Patent: Feb. 21, 1995

[54] USE OF AN ENZYME CONTAINING GRANULATE IN A METHOD FOR PRODUCTION OF A PELLETIZED FODDER

[75] Inventors: Kim T. Jacobsen, Greve Strand; Poul E. Jensen, Allerod, both of Denmark

[73] Assignee: Novo Nordisk A/S, Bagsvaerd, Denmark

[21] Appl. No.: 70,402

[22] PCT Filed: Jan. 24, 1992

[86] PCT No.: PCT/DK92/00026
§ 371 Date: Jun. 4, 1993
§ 102(e) Date: Jun. 4, 1993

[87] PCT Pub. No.: WO92/12645
PCT Pub. Date: Aug. 6, 1992

[30] Foreign Application Priority Data

Jan. 25, 1991 [DK] Denmark ............................ 134/91

[51] Int. Cl.⁶ ............................................ A61K 37/48

[52] U.S. Cl. .................................. 424/94.2; 424/94.1; 424/94.3; 424/94.4; 424/94.5; 424/94.6; 424/94.61; 424/94.62; 424/94.63; 424/94.64; 424/94.65; 424/94.66; 424/94.67; 424/499; 424/497; 426/2; 426/63; 426/454; 426/463; 424/499; 424/497

[58] Field of Search .............. 424/94.1, 94.2, 94.3, 424/94.4, 94.5, 94.6–94.67, 499, 497; 426/2, 63, 454, 463, 636, 640, 615

[56] References Cited

FOREIGN PATENT DOCUMENTS

| | | |
|---|---|---|
| 0113626 | 7/1984 | European Pat. Off. |
| 0257996 | 3/1988 | European Pat. Off. |
| 0276781 | 8/1988 | European Pat. Off. |
| 0304332 | 2/1989 | European Pat. Off. |
| 3520007 | 12/1985 | Germany. |
| 2167758 | 6/1986 | United Kingdom. |
| WO89/08694 | 9/1989 | WIPO. |

*Primary Examiner*—Douglas W. Robinson
*Assistant Examiner*—Jean C. Witz
*Attorney, Agent, or Firm*—Steve T. Zelson; Karen A. Lowney

[57] ABSTRACT

An enzyme containing T-granulate, coated with a coating agent comprising a high melting fat or wax, is combined with a mixture containing fodder components, and the combination is steam treated and subsequently pelletized. The method considerably improves the stability of the enzyme in the pelletized mixture.

13 Claims, No Drawings

USE OF AN ENZYME CONTAINING GRANULATE IN A METHOD FOR PRODUCTION OF A PELLETIZED FODDER

The invention comprises a use of an enzyme containing granulate and a method for production of a pelletized fodder.

In the art comprising fodder it is described that the addition of enzymes to the fodder has a beneficial effect, vide e.g. Hesselman, K. and Åman P., The effect of β-glucanase on the utilization of starch and nitrogen by broiler chickens fed on barley of low- or high-viscosity. Animal Feed Science and Technology, 15 (1986) 83–93. Also, in the art comprising fodder it is a well known fact that pelletizing of the fodder is a desideratum, as pelletizing of the fodder increases the digestibility of especially the starch fraction. Furthermore, pelletizing of the fodder reduces the dust, it makes the fodder easier to eat for the birds, and it makes it possible to incorporate small amounts of ingredients in the fodder and to "lock" the fodder mixture. In the process of producing fodder pellets it is considered necessary to heat treat the fodder pellets in order to kill the Salmonella bacteria, whereby a heat treatment to around 80° C. is appropriate. The enzymes are not stable at this high temperature, and thus, a large surplus of enzymes has to be used, or enzyme free fodder components have been pelletized and heat treated, whereafter an enzyme containing slurry or solution has been coated on the heat treated pellets. However, this coating is cumbersome and is often not compatible with existing plants. Thus, there is a need for an enzyme containing fodder which can be produced easier and by means of existing fodder producing plants.

The art encompassing enzyme containing granulates produced as additives in detergents comprises a so-called T-granulate, produced as indicated in U.S. Pat. No. 4,106,991. A T-granulate which is coated with a wax, a triglyceride or other fat, is described in WO 89/08694, claims 12 and 1, EP 206,417, claims 17, 13, and 1, and U.S. Pat. No. 4,707,287, claims 1 and 14 and column 9, example II.

This coated T-granulate has been produced by coating of the T-granulate by a triglyceride instead of the traditional PEG.

The above indicated, coated T-granulate is used as an additive in detergents, and to the best of applicant's knowledge this coated T-granulate has not been suggested for other uses than in the detergent field.

Surprisingly, according to the invention, it has now been found that the above indicated T-granulate can be used as a component of a mixture, which can be converted to a fodder by treatment with steam and pelletizing without appreciable loss of enzyme activity, in contradistinction to the prior art, in relation to which an appreciable loss of enzyme activity will take place during steam treatment and pelletizing.

Thus, the use according to the invention of an enzyme containing T-granulate which is coated with a coating agent comprising a high melting fat or wax, is a use as a component of a mixture, which is well suited as a fodder if the mixture is steam treated and subsequently pelletized.

A T-granulate is a granulate produced according to U.S. Pat. No. 4,106,991, i.e. a granulate containing 2–40% finely divided cellulose fibres. Also, it is to be understood that the T-granulate contains one or more of the enzymes, which can be used as additives to fodders. As typical examples can be mentioned: proteases, e.g. from Bacillus, for instance *Bacillus licheniformis,* xylanases, cellulases, beta-glucanases, e.g. from Bacillus, Humicola, for instance *Humicola insolens,* or Actinomycetes, pectinases, e.g. from Aspergillus, α-galactosidases, e.g. from Aspergillus, for instance *Aspergillus niger,* and amylases, e.g. from Bacillus, for instance *Bacillus subtills.*

The coating agent comprises a high melting fat or wax. in this specification with claims a high melting fat is a glycerol ester (mono-, di- or triester or a mixture thereof) with a melting point between 30° and 100° C., and a high melting wax is a waxy substance according to the definition in U.S. Pat. No. 4,106,991, col. 3, lines 45–50, i.e. a substance which possesses all of the following characteristics: (1) the melting point is between 30° and 100° C., preferably between 40° and 60° C., (2) the substance is of tough and not brittle nature, and (3) the substance possesses substantial plasticity at room temperature.

It appears from the applicant's EP 304,332 that the stability of the enzymes and the physical strength of the granules is improved, if a core is provided with a coating of cellulose fibres, a binder, an enzyme, a filler and a waxy material. It appears from DK 161717 that β-glucanases or α-amylases can be stabilized by adhesion to a solid carrier; such preparations can be used as ingredients in granulated fodders. It also appears from DE 3,520,007 and GB 2,167,758 that enzyme containing granulates can be coated with fats or waxes. On the basis of this prior art it apparently can be concluded that it is obvious that enzyme containing granulates coated with fat or wax in general are well suited as a component of a fodder mixture to be pelletized. This conclusion, however, is false, as it has been found that some enzyme containing granulates coated with fat or wax (e.g. fat coated Bio-Feed Plus, later to be characterized) are not well suited as a component of a fodder mixture to be pelletized.

Thus it is surprising that the use according to the invention gives rise to a stable fodder, because it already belongs to the prior art that Bio-Feed Plus (fraction of wheat coated with enzymes), fat coated Bio-Feed Plus, T-granulate not fat coated, and Cellulase P (prill enzyme preparation with high fat content) as a component of a mixture which is converted into a fodder does not give rise to a fodder with stable enzyme activity. These prior art phenomena will be documented later in this specification.

A preferred embodiment of the use according to the invention is characterized by the fact that the coating agent comprises up to 80%, preferably 60–75% of a filler, which is a dry powder of any material, preferably an inorganic material, more preferably kaolin, magnesium silicate or calcium carbonate. Incorporation of the indicated filler into the coating agent in the amount indicated will reduce the tendency of the separate granules to adhere to each other and to the granulating apparatus.

A preferred embodiment of the use according to the invention is characterized by the fact that the coating agent constitutes 1–95% w/w, preferably 15–35% w/w of the final, coated T-granulate. If an amount of coating agent below 1% w/w is used no satisfactory enzyme stability improvement is obtained, and if an amount of coating agent above 95% is used, no further improvement of the enzyme stability is obtained.

A preferred embodiment of the use according to the invention is characterized by the fact that the T-granulate on top of the coating is coated once more with a polymeric material, preferably in a fluidized bed. In this manner the enzymatic stability is further improved.

Also the invention comprises a method for production of a pelletized fodder, and this method is characterized by the fact that a mixture of an enzyme containing T-granulate, which is coated with a coating agent comprising a high melting fat or wax, and fodder components, is steam treated and subseqently pelletized.

A preferred embodiment of the method according to the invention is characterized by the fact that the coating agent comprises up to 80%, preferably 60–75 % of a filler, which is a dry powder of any material, preferably an inorganic material, more preferably kaolin, magnesium silicate or calcium carbonate. Incorporation of the indicated filler into the coating agent in the amount indicated will reduce the tendency of the separate granules in the T-granulate to adhere to each other and to the granulating apparatus.

A preferred embodiment of the method according to the invention is characterized by the fact that the coating agent constitutes 1–95% w/w, preferably 15–35% w/w of the final, coated T-granulate. If an amount of coating agent below 1% w/w is used no satisfactory enzyme stability improvement is obtained, and if an amount of coating agent above 95% is used, no further improvement of the enzyme stability is obtained.

A preferred embodiment of the method according to the invention is characterized by the fact that the T-granulate on top of the coating is coated once more with a polymeric material, preferably in a fluidized bed. In this manner the enzymatic stability is further improved.

The following examples illustrate the invention.

Example 1 illustrates the use and the method according to the invention.

Example 2 illustrates a further advantage of the use according to the invention in relation to in vivo conditions.

EXAMPLE 1

This example illustrates the use according to the invention and the method according to the invention, in comparison to the prior art most related thereto.

The enzyme containing T-granulate related to both the use according to the invention and the method according to the invention is produced in the following manner, the granulate being identified as Bio-Feed Plus T.

The powder components for 20 kg of granulate are the following:

2.0 kg of cellulose ARBOCEL BC 200
13.6 kg of ground sodium sulfate
0.6 kg of carbohydrate binder
1.2 kg of chalk The above components are mixed in a 50 liter Lödige mixer, with heating to 35° C. The mixing time is 2 minutes at a mixing velocity of the mixer paddles of 145 rpm and a knife rotating velocity of 3000 rpm.

Under the above indicated conditions 6.4 kg of liquid cellulase concentrate (dry matter 40%, cellulase activity 764 EGU/g, the EGU activity unit being defined in AF-275, is sprinkled on the mixture. The sprinkling is performed by means of an atomizing nozzle and with a sprinkling time of around 6 minutes.

Subsequently the wet mixture is subjected to a further granulation for 2 minutes, until uniform sphere or lens formed granulates are obtained.

The humid granulate is dried in a fluid bed at an inlet temperature of 60° C., until a water content of less than 3% is obtained.

The particle size distribution of the dry granulate was:

| | |
|---|---|
| >1200 μm | 9.5% |
| >1000 μm | 15.3% |
| >850 μm | 23.8% |
| >707 μm | 36.3% |
| >600 μm | 51.1% |
| >500 μm | 66.4% |
| >420 μm | 73.8% |
| >300 μm | 88.9% |
| <250 μm | 3.7% |

The activity loss was less than 5%.

Subsequently the dry granulate is coated with a total of 20 weight-% of hydrogenated beef tallow and 15.5 weight-% of magnesium silicate, in the following manner. The dry, raw granulate is heated to 65° C., and subsequently 5 weight-% of hydrogenated beef tallow heated to 70° C. is applied thereto, and thereafter 5.17% of magnesium silicate is applied thereto. These operations are repeated until the total amounts of hydrogenated beef tallow and magnesium silicate are added.

Then the granulate is cooled. Now the granulate is ready for use.

The following enzyme containing granulates representing the prior art most related to the invention were used as comparison granulates.

1) Bio-Feed Plus. This is a granulate consisting of a fraction of wheat coated with enzymes. Reference can be made to the brochure B402c-GB 1500 Oct. 1990.
2) Bio-Feed Plus, tallow coated. This is Bio-Feed Plus coated with hydrogenated beef tallow in an amount of 20%
3) Cellulase T. This is a T-granulate with a fungal beta-glucanase and a cellulase, manufactured as indicated above in relation to the manufacture of Bio-Feed Plus T, except for the fact that the coating is omitted
4) Cellulase P. This is a prill product with a fungal beta-glucanase and a cellulase. This product is prepared by mixing a melted fat with the spray dried enzymes. The mixture of melted fat and the spray dried enzymes is sprayed into a chilled air stream, whereby the fat solidifies as droplets, whereby the enzymes are encapsulated in the fat. Reference can be made to the brochure B 495a-GB Jul. 1989.

These four reference granulates and the granulate used according to the invention were used for production of a pelletized fodder as follows.

The composition of the fodder for small pigs were the following.

7% fish meal
15% soy bean flakes
62% wheat
10% barley
2% animal fat
minerals+vitamins The animal fat was industrial waste fat.

The minerals+vitamins were added in the following amounts, calculated on 1 g of fodder:

50 μg of Olaquindox
100 μg of Toyocerin
16 i.u. of vitamin A
2 i.u. of vitamin $D_3$
130 μg of vitamin E
4 μg of vitamin $B_2$
20 μg of nicotinic acid
15 μg of D-pantothenic acid
0.02 μg of vitaimin $B_{12}$
0.2 μg of biotin
2 μg of vitamin $B_1$
2 μg of vitamin $B_6$
2 μg of vitamin $K_3$
100 μg choline chloride
25 μg Mn (manganese)
234 μg Fe (iron)
163 μg Cu (copper)
200 μg Zn (zinc)
0.3 μg J (iodine)
0.3 μg Se (selenium)

The first four components of the above fodder for small pigs were mixed in a mill on a sieve with apertures of 2.0 mm, and then mixed with the two last components of the above fodder for small pigs in a 2500 liter horizontal mixer. The finished meal mixture was used for the experiments in a pilot plant with batches of 100 kg.

In each experiment 10 kg of the above finished meal was mixed with 2 kg of any of the above indicated five granulates for 10 minutes in order to produce a premix. Then 88 kg of the above finished meal was mixed with the 12 kg of premix, thereby producing 100 kg of a mixture to be pelletized. The pelletizing procedure was performed at 70° C. and with direct steam injection to a weight increase of 4%. The pelletizing process lasted for 25-30 seconds. Subsequently the pellets were cooled down to ambient temperature, and the pelletized product is now stable in regard to enzyme activity. The loss of enzyme activity takes place exclusively during the pelletizing process.

Determinations of residual activity were now carried out in regard to the five different pelletized materials. The results appear from the following table, in which FBG is fungal beta-glucanase, vide AF 70.1/2-GB.

|  | Enzyme granulate in fodder pellets | % residual FBG activity |
|---|---|---|
| Prior art | Bio-Feed Plus | 75 |
|  | Bio-Feed Plus, tallow coated | 75 |
|  | Cellulose T | <30 |
|  | Cellulose P | 50 |
| Invention | Bio-Feed Plus T | 90-100 |

It clearly appears from the above table that the use and the method according to the invention is superior to the prior art uses and methods most closely related to the invention.

EXAMPLE 2

This example illustrates an additional advantage of the use according to the invention compared to a traditionally used enzyme containing product, when used in a fodder for pigs.

Most enzymes are lablie in acid environment and/or under the influence of proteolytic activity. Thus when adding enzymes to animal fodder a significant loss of enzyme activity can often be expected after ingestion, when subjected to gastric conditions.

To achieve the optimal benefit of the added enzymes a good survival of enzyme activity from the gastric environment is necessary to prolong the effect of the enzymes over the gastro-intestinal tract.

In the two feeding experiments in this example the technique of reentrant cannulation of a grown pig of approx. 50 kg was used. Reference can be made to Horszczaruk. F. et al., "Roczniki nauk Rolniczych" 95 B4, 69-77 (1974) and Rainbird, A. L. et al., British Journal of Nutrition (1984), 52, 89-498, Effect of guar gum on glucose and water absorption from isolated loopes of jejenum in conscious growing pigs.

This technique enables the estimation of the survival of enzyme activity after ingestion and passing through part of the gastro-intestinal tract of the pig.

The enzyme containing coated T-granulate was produced as indicated in U.S. Pat. No. 4,106,991 by mixing sodium sulphate, cellulose, kaolin and dextrin in a high energy Lödige Mixer whereafter a liquid enzyme concentrate which was previously adjusted to approx. 700 EGU/g was sprayed onto the mixture whereby the proportions of sodium sulphate, cellulose, kaolin, dextrin and enzyme dry matter corresponds to the figures indicated below, and the amount of added water was just enough to generate correct granulation consistency and particle size distribution (reference being made to U.S. Pat. No. 4,106,991, col. 2, lines 8-12).

After granulation the product was transferred to a fluidized bed and dried with hot air to reduce the water content to 1.0% (w/w).

In the T-granulate thus produced the percentage concentration (w/w) of the above dry ingredients were as follows:

| Sodium sulphate | 71.0% |
|---|---|
| cellulose | 8.9% |
| kaolin | 3.0% |
| dextrin | 5.0% |
| enzyme dry matter | 11.1% |

After drying the T-granulate was fractionated by sieving to a particle size between 300 μm and 1180 μm with respect to the particle diameter.

The T-granulate was then coated in a coating mixer by spraying with hydrogenated beef tallow and a filler, which is a premixed blend of equal parts of kaolin and calcium carbonate, in an alternate fashion. The coating was performed as follows. First (in percentage of the uncoated T-granulate) 4% (w/w) of hydrogenated beef tallow was sprayed onto the mix, followed by addition of 12.5% (w/w) of the filler. This was followed by an analogous coating with 4% (w/w) hydrogenated beef tallow and 12.5% of the filler. A final coating with 1.5% hydrogenated beef tallow concluded the coating procedure.

After the coating the warm coated T-granualte was cooled in a fluidized bed with air at ambient temperature. During this process fines were removed.

The cooled enzyme containing coated T-granulate was finally fractionated by sieving to secure a particle size of between 300 μm and 1180 μm.

The composition of the enzyme free fodder used in the feeding experiments was:

| Oat bran: | 67.71% (w/w) |
|---|---|

| | |
|---|---|
| Toasted soy flakes: | 15.00% (w/w) |
| Wheat starch: | 15.09% (w/w) |
| Vitamin/mineral mix: | 2.20% (w/w) |

Formally, the uses and the methods described in this example are not inside the scope of the invention, because the fodder is not pelletized. However, due to the fact that a comparison is made between a coated T-granulate, which can be used according to the invention, and a granulate, which cannot be used according to the invention, the example will demonstrate an advantage of the use and method according to the invention over the prior art.

The reentrant cannulated pig which was used in the experiments was in both cases fed with a total of 610 g dry fodder as described above, mixed with 1525 g of water, as a single meal. Two enzyme preparations were investigated: 1) "Bio-Feed Plus, coated T-granulate" produced as described above (according to the invention), and 2) "Bio-Feed Plus", a traditional product where the enzyme is coated onto a manna grit carrier (prior art). Reference is made to the brochure B 402c-GB 1500, Oct. 1990.

In the first experiment 9.15 g of "Bio-Feed Plus, coated T-granulate" was also added to the fodder and in the second experiment 6.1 g of "Bio-Feed Plus" was also added to the fodder, whereby the different gravimetric dosages correspond to equal dosages of enzyme activity.

In both cases the enzyme products were first mixed with the water and then mixed thoroughly with the dry fodder to ensure a homogenous mixture.

A small representative sample of this mixture was removed and freeze dried for later determination of enzyme activity in the fodder.

In these experiments the reentrant cannula was placed in the pig's small intestine approx. 3 m distal to the pancreatic gland.

Beginning immediately after the ingestion by the animal of the full amount of the fodder the total intestinal content was continuously collected from the open cannula in separate pools. From each pool a representative sample of 15% was collected and freeze dried for later analysis. Then the remaining intestinal content after being heated to 40° C. was pumped back to the intestine through the other half of the reentrant cannula.

After analyzing the specific beta-glucanase, pentosanase and xylanase activity in the samples obtained as described above the total survival of these exogenic enzyme actitivies can be calculated.

Before analysis the samples were extracted in the relevant buffer for each analysis by mixing 1 part of sample with 4 parts of buffer and stirring vigorously for 30 minutes. Subsequently the samples were centrifuged for 10 minutes at 3000 rpm, and the supernatant removed for analysis.

Glucanase activity was determined according to the procedure AF 295/1-GB type feed.

Xylanase activity was determined according to the procedure AF 293.6.1-GB.

Pentosanase activity was determined according to the procedure AF 284/1-GB.

The results of the analysis is shown in the following table, which shows the total accumulated enzyme activity reaching the cannula in the small intestine eight hours after the feeding, indicated in percentage of the enzyme activity in the feed mix ingested by the animal.

| | Residual Glucanase Activity (%) | Residual Xylanase Activity (%) | Residual Pentosanase Activity (%) |
|---|---|---|---|
| Bio-Feed Plus, coated T-granulate | 52 | 50 | 60 |
| Bio-Feed Plus | 28 | 27 | 38 |

It is thus surprisingly found that the residual glucanase, xylanase, and pentosanase activity in the first part of the pig's small intestine is significantly higher according to the invention than according to the prior art.

The brochures and the AF documents referred to above are obtainable on request from Novo Nordisk A/S, Novo Allé, DK-2880 Bagsvaerd, Denmark.

We claim:

1. A method for the manufacture of a pelletized fodder, the method comprising the following subsequent steps:
   (a) mixing one or more fodder components with an enzyme containing T-granulate, which granulate is coated with a coating agent comprising a high melting fat or a high melting wax;
   (b) subjecting the mixture to a steam treatment; and
   (c) pelletizing the steam treated mixture.

2. The method according to claim 1, wherein the enzyme containing granulate comprises one or more enzymes selected from the group consisting of a protease, a xylanase, a cellulase, a beta-glucanase, a pectinase, an alpha-galactosidase, and an amylase.

3. The method according to claim 1, wherein the enzyme containing granulate comprises 2–40% w/w of cellulose fibre.

4. The method according to claim 1, wherein the high melting fat is a glycerol mono-, di- or triester, or a mixture thereof having a melting point between 30° and 100° C.

5. The method according to claim 1 wherein the high melting wax has a melting point between 30° and 100° C.

6. The method according to claim 5, wherein the high melting wax is tallow.

7. The method according to claim 5, wherein the high melting wax is hydrogenated beef tallow.

8. The method according to claim 1, wherein the coating agent further comprises up to 80% w/w of a filler.

9. The method according to claim 8, wherein the coating agent further comprises 60–75% w/w of a filler.

10. The method according to claim 8, wherein the filler is selected from the group consisting of kaolin, magnesium silicate and calcium carbonate.

11. The method according to claim 1, wherein the coating agent constitutes 1–95% w/w of the granulate.

12. The method according to claim 1, wherein the coating agent constitutes 15–35% w/w of the granulate.

13. The method according to claim 1, wherein the fodder components are selected from the group consisting of fish meal, soy bean flakes, toasted soy flakes, oat bran, wheat, wheat starch, barley, animal fat, minerals, and vitamins.

* * * * *